United States Patent [19]

Klaveness et al.

[11] Patent Number: 5,208,324

[45] Date of Patent: May 4, 1993

[54] PARAMAGNETIC COMPOUNDS

[75] Inventors: Jo Klaveness, Oslo; Pal Rongved, Hellvik; Per Strande, Oslo, all of Norway

[73] Assignee: Nycomed Imaging AS, Oslo, Norway

[21] Appl. No.: 548,994

[22] PCT Filed: Jan. 26, 1989

[86] PCT No.: PCT/EP89/00078

§ 371 Date: Jul. 26, 1990

§ 102(e) Date: Jul. 26, 1990

[87] PCT Pub. No.: WO89/06979

PCT Pub. Date: Aug. 10, 1989

[30] Foreign Application Priority Data

Jan. 26, 1988 [GB] United Kingdom ............... 8801646

[51] Int. Cl.$^5$ ............................................. A61K 49/00
[52] U.S. Cl. ...................................... 534/16; 424/1.1;
424/9; 534/15; 436/173; 530/391.5; 536/17.1;
536/51; 536/101; 536/112; 536/113; 536/121
[58] Field of Search ............... 534/10, 15, 16; 424/9,
424/1.1, 85; 436/173; 530/391.5; 536/17.1, 51,
101, 112, 113, 121

[56] References Cited

U.S. PATENT DOCUMENTS

| | | |
|---|---|---|
| 4,124,705 | 11/1978 | Rothman et al. |
| 4,615,879 | 10/1986 | Runge et al. |
| 4,639,365 | 1/1987 | Sherry |
| 4,687,659 | 8/1987 | Quay |
| 4,699,784 | 10/1987 | Shih et al. ............... 424/85 |
| 4,714,607 | 12/1987 | Klaveness |
| 4,741,900 | 5/1988 | Alvarez et al. ............. 424/85 |
| 4,985,233 | 1/1991 | Klaveness et al. ............ 424/9 |
| 4,986,980 | 1/1991 | Jacobsen .................. 424/9 |
| 5,047,227 | 9/1991 | Rodwell et al. ........... 424/1.1 |
| 5,057,313 | 10/1991 | Shih et al. ............. 424/85.91 |

FOREIGN PATENT DOCUMENTS

| | | |
|---|---|---|
| 86330/82 | 1/1983 | Australia. |
| 76217/87 | 2/1988 | Australia. |
| 14611/88 | 10/1988 | Australia. |
| 1253514 | 5/1989 | Canada. |
| 0136812 | 4/1985 | European Pat. Off. |
| 0184899 | 6/1986 | European Pat. Off. |
| 0186947 | 7/1986 | European Pat. Off. |
| 0230893 | 8/1987 | European Pat. Off. |
| 0232751 | 8/1987 | European Pat. Off. |
| 0292689 | 11/1988 | European Pat. Off. |
| WO86/02352 | 4/1985 | Int'l Pat. Institute. |
| WO85/05554 | 12/1985 | Int'l Pat. Institute. |
| WO86/02005 | 4/1986 | Int'l Pat. Institute. |
| WO87/01594 | 3/1987 | Int'l Pat. Institute. |
| WO87/02893 | 5/1987 | Int'l Pat. Institute. |
| WO89/00557 | 1/1989 | Int'l Pat. Institute. |
| 2137612A | 10/1984 | United Kingdom. |

OTHER PUBLICATIONS

Runge et al., "Paramagnetic Agents for Contrast-Enhanced NMR Imaging: A Review", 1983, pp. 1209-1215.

Mendonca-Dias et al., "Paramagnetic Contrast Agents in Nuclear Magnetic Resonance Medical Imaging", Seminars in Nuclear Medicine, vol. XIII, No. 4, Oct., 1984, pp. 364-376.

Brasch, "Work in Progress: Method of Contrast Enhancement for NMR Imaging and Potential Applications", 1983, pp. 781-788.

Koutcher, et al, "Adjunctive Medical Knowledge", The Journal of Nuclear Medicine, vol. 25, No. 4, 1984, pp. 506-513.

Schmiedl et al., "Albumin Labeled with Gd-DTPA as an Intravascular, Blood Pool—Enhancing Agent for MR Imaging: Biodistribution and Imaging Studies", 1987, pp. 205-210.

Weinmann et al., "Characteristics of Gadolinium-DTPA Complex: A Potential NMR Contrast Agent", 1984, pp. 619-624.

Runge et al., "Work in Progress: Potential Oral and Intravenous Paramagnetic NMR Contrast Agents", 1983, pp. 789-791.

Doyle et al., "Nuclear Magnetic Resonance (NMR) Imaging Symposium", Journal of Computer Assessed Tomography, vol. 5, No. 2, 1981, pp. 295-296.

Lauterbur, "Progress in n.m.r. zeugmatographic imaging", Phil. Trans. R. Soc. Lond. B 289, 1980, pp. 483-487.

Lauterbur, et al., "Augmentation of Tissue Water Proton Spin-Lattice Relaxation Rates by in vito Addition of Paramagnetic Ions", 1978, pp. 752-759.

*Primary Examiner*—Robert L. Stoll
*Assistant Examiner*—C. Sayala
*Attorney, Agent, or Firm*—Bacon & Thomas

[57] ABSTRACT

There are provided paramagnetic compounds comprising a paramagnetic metal species chelated by a chelating moiety bound by an amide group to a linker group itself bound by an ester group to a macromolecule, wherein said linker group provides a carbon chain of at least 2 atoms between said amide group and said ester group. The novel compounds are particularly suitable as contrast agents, e.g. in magnetic resonance imaging.

18 Claims, No Drawings

PARAMAGNETIC COMPOUNDS

The present invention relates to macromolecular paramagnetic compounds, to contrast agents containing such compounds and their use in magnetic resonance imaging (MRI) of human and non-human subjects, to chelating agents for use in the manufacture of such compounds and to the use of such chelating agents and chelates and and salts thereof in therapy and diagnosis.

In MRI, the contrast in the images generated may be enhanced by introducing into the zone being imaged an agent which affects the spin reequilibration characteristics of the nuclei (the "imaging nuclei", which are generally protons and more especially water protons) which are responsible for the resonance signals from which the images are generated. In this respect it has been found that contrast enhancement results from the use of contrast agents containing paramagnetic, superparamagnetic or ferromagnetic species. For paramagnetic contrast agents, the enhanced image contrast derives predominantly from the reduction in the spin reequilibration coefficient known as $T_1$ or as the spin-lattice relaxation time, a reduction which arises from the effect on the imaging nuclei of the fields generated by the paramagnetic centres.

The use of paramagnetic compounds as contrast agents in MRI has been widely advocated and a broad range of paramagnetic compounds has been suggested in this regard. Thus for example Lauterbur and others have suggested the use of manganese salts and other paramagnetic inorganic salts and complexes (see Lauterbur et al. in "Frontiers of Biological Energetics", volume 1, pages 752-759, Academic Press (1978), Lauterbur in Phil. Trans. R. Soc. Lond. B 289: 483-487 (1980) and Doyle et al. in J. Comput. Assist. Tomogr. 5(2): 295-296 (1981)), Runge et al. have suggested the use of particulate gadolinium oxalate (see U.S. Pat. No. 4,615,879 and Radiology 147(3): 789-791 (1983)), Schering AG have suggested the use of paramagnetic metal chelates, for example of aminopolycarboxylic acids such as nitrilotriacetic acid (NTA), N,N,N',N'-ethylenediaminetetraacetic acid (EDTA), N-hydroxyethyl-N,N',N'-ethylenediaminetriacetic acid (HEDTA), N,N,N',N'',N''-diethylenetriaminepentaacetic acid (DTPA) and 1,4,7,10-tetraazacyclododecanetetraacetic acid (DOTA) (see for example EP-A-71564, EP-A-130934 and DE-A-3401052), and Nycomed AS have suggested the use of paramagnetic metal chelates of iminodiacetic acids (see EP-A-165728). Many other paramagnetic contrast agents have been suggested in the literature, for example in EP-A-230893, EP-A-232751, EP-A-292689, EP-A-255471, EP-A-292689, EP-A-287465, U.S. Pat. No. 4,687,659 and WO86/02005. Besides the chelates of DOTA and DTPA, the chelates of N,N" (bis methyl-carbamoyl-methyl) N,N',N"-diethylenetriamine triacetic acid (DTPA-BMA), 1-oxa-4,710-triazacyclododecane-N,N',N"-triacetic acid (OTTA) and N-[2,3-dihydroxy-N-methyl-propylcarbamoylmethyl]-1,4,7,10-tetraazacyclododecane-N',N",N'''-triacetic acid, etc. (DO3A) deserve particular mention.

Paramagnetic compounds in which the paramagnetic centre is bound in a chelate complex have been considered particularly desirable as otherwise toxic heavy metals, such as gadolinium for example, may in this way be presented in a biotolerable form. The use of chelating agents, such as EDTA, DTPA, etc., known for their efficacy as heavy metal detoxification agents has thus received particular attention (see for example Weinmann et al., In AJR 142: 619-624 (1984)).

While the toxicities of the paramagnetic chelates are generally lower than those of the inorganic salts of the same paramagnetic metal species, the efficiency of such chelate complexes in contrast enhancement is not greatly improved relative to that of the salts.

It has however been found that by binding the paramagnetic species to a relatively heavy carrier, for example a macromolecule, increased contrast effect can be achieved, perhaps at least in part due to the effect of the heavy carrier in slowing down tumbling motions of the paramagnetic species. This is well illustrated by Technicare Corporation in EP-A-136812. Binding macromolecules to paramagnetic compounds has also been suggested as a means by which tissue-specific paramagnetic contrast agents can be produced. Thus, for example, Schering AG in EP-A-71564, suggest binding paramagnetic chelates to biomolecules such as hormones, proteins and the like to cause the contrast agent after administration to congregate at particular body sites. Technicare Corporation, in EP-A-136812, similarly suggest binding paramagnetic ions to tissue-specific macromolecules such as, for example, antibodies.

Binding paramagnetic chelates to albumin to produce a blood pooling contrast agent has also been suggested and one such compound, Gd DTPA-albumin, is discussed by Schmiedl et al. in Radiology 162:205 (1987). Proteins such as albumin are substances of very complicated structure and generally possess limited stability. In particular, protein bound substances are difficult to formulate into solutions and should not be subjected to heat treatment, and thus contrast agents containing such substances cannot be sterilized by the application of heat. Furthermore, to reduce the risk of allergic response it would generally be appropriate to utilize a human-derived protein, e.g. human albumin, and thus a possible risk of viral contamination from the human source arises. Consequently, Nycomed As, in EP-A-184899 and EP-A-186947, suggested MRI contrast agents comprising paramagnetic chelates associated with thermostable, readily characterized, biologically relatively passive macromolecules such as polysaccharides, e.g. dextrans. Thus EP-A-186947 discloses soluble macromolecular paramagnetic compounds which where they have molecular weights above the kidney threshold may function as blood pooling MRI contrast agents.

Amersham International PLC have also suggested, in WO85/05554, the use of macromolecular carriers for paramagnetic chelates for use as MRI contrast agents. However, stressing the importance that the chelate complex must be stable in vivo (in particular where the paramagnetic metal ion itself is toxic) Amersham have suggested that the possibility of the macromolecule sterically hindering chelation of the paramagnetic metal species by the chelating entity may be avoided by binding the chelating entity to the macromolecule through the agency of a linker molecule, for example to produce the compound X—OCONH—$(CH_2)_n$—NHCO—Y, where X is the macromolecule and Y is the chelating entity. One such chelate-linker-macromolecule compound, GdDOTA-glycine-dextran, is also disclosed in EP-A-186947.

Other paramagnetic MRI contrast agents are disclosed in the literature (see for example WO87/02893, U.S. Pat. No. 4,639,365 and WO87/01594 and the references listed in these documents) and there have been several reviews of paramagnetic MRI contrast agents (see for example AJR 141: 1209-1215 (1983), Sem. Nucl. Med. 13: 364 (1983), Radiology 147: 781 (1983) and J. Nucl. Med. 25: 506 (1984)).

When a paramagnetic compound is administered into the cardiovascular system of a subject to be imaged, the fate of the compound depends on a number of factors. If it comprises insoluble particulate matter, it will be removed from the blood system by the reticuloendothelial system (RES), in particular by Kupffer cells of the liver; if it contains relatively large particles, such as liposomes, these may lodge in the lungs; and if the compound is soluble and of relatively low molecular weight it may be cleared out of the blood through the kidneys relatively rapidly (as is the case with GdDTPA-dimeglumine, an agent developed and tested by Schering AG). Thus GdDTPA-dimeglumine has a half life in the blood of about 20 minutes (see Weinmann et al. in AJR 142: 619-624 (1984)).

However for a paramagnetic MRI contrast agent to be suitable as a blood pooling agent, i.e. one which is not rapidly removed from the cardiovascular system, it is necessary that the paramagnetic compound be soluble, that it should have a molecular weight sufficiently high as to prevent rapid excretion through the kidneys, and that it should have an in vivo stability which achieves a balance between the stability required to ensure adequate half life in the blood pool and the instability required for the compound, or more particularly the paramagnetic species contained therein, to be excretable.

We have now found that by the use of a linker moiety which is bound to the macromolecule by an ester grouping and to the chelating moiety by an amide grouping and which provides a carbon chain of at least 2 atoms in length between the ester and amide groups, it is possible to provide macromolecular paramagnetic MRI contrast agents with improved properties, in particular for the imaging of the cardiovascular system. More particularly, we have found that by the use of such linker moieties a particularly desirable balance between in vivo stability and in vivo instability is achieved.

Thus in one aspect the present invention provides a paramagnetic compound comprising a paramagnetic metal species chelated by a chelating moiety bound by an amide group to a linker group itself bound by an ester group to a macromolecule, wherein said linker group provides a carbon chain of from 2 to 11 atoms between said amide group and said ester group.

The linker group in the paramagnetic compounds of the present invention is preferably the residue of an amino acid of formula I

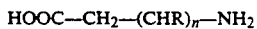  (I)

(wherein, n is an integer of from 1 to 10, and each R, which may be the same or different, represents a hydrogen atom or a hydroxyl, hydroxyalkyl, or $C_{1-4}$ alkyl group, with the proviso that R on the carbon attached to the amine group does not represent a hydroxyl group).

In formula I above, n is preferably an integer of from 1 to 6, an especially preferably from 1 to 3, and R is preferably hydrogen, methyl, ethyl, hydroxyl, mono- or poly-hydroxy ($C_{1-6}$ alkyl), especially mono- or poly-hydroxy ($C_{1-4}$ alkyl), for example hydroxymethyl or 2,3-dihydroxy-propyl. Where R is a polyhydroxyalkyl group, the ratio of hydroxyl groups to carbon atoms is preferably up to 1:1. Residues of compounds of formula I in which n is from 1 to 10 and R is hydrogen also are preferred as the linker group in the paramagnetic compounds of the invention. Particularly preferred identities for the linker group include the residues of beta and gamma amino acids, for example beta-alanine and 4-amino-butanoic acid.

The chelating moiety in the paramagnetic compounds of the present invention may conveniently be the residue of a conventional metal chelating agent. Suitable such agents are well known from the literature relating to MRI contrast agents discussed above (see for example EP-A-71564, EP-A-130934, EP-A-186947, U.S. Pat. No. 4,639,365, EP-A-230893, EP-A-232751, EP-A-292689, EP-A-255471, U.S. Pat. No. 4,687,659, WO-86/02005 and DE-A-3401052) as well as from the literature relating to chelating agents for heavy metal detoxification.

The chelating moiety chosen should clearly be one that is stable in vivo and is capable of forming a chelate complex with the selected paramagnetic species. Preferably however, the chelating moiety will be one as described in EP-A-186947 or the residue of an aminopoly (carboxylic acid or carboxylic acid derivative) (hereinafter an APCA) or a salt thereof, for example one of those discussed by Schering AG in EP-A-71564, EP-A-130934 and DE-A-3401052 and by Nycomed AS in International Patent Application No. PCT/GB88/00572. This latter application discloses APCAs which carry hydrophilic groups, e.g. on the amine nitrogens or on the alkylene chains linking the amine nitrogens, for example compounds of formula II

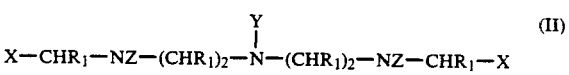  (II)

(wherein each of the groups Z is a group —$CHR_1X$ or the groups Z are together a group —$(CHR_1)_2$—$A'$—$(CHR_1)_2$, where $A'$ is O, S, N—$CHR_1X$ or N—$(CHR_1)_p$—$N(CHR_1X)_2$ where p is 2, 3 or 4; Y is a group —$(CHR_1)_2$—$N(CHR_1X)_2$ or a group —$CHR_1X$; each X, which may be the same or different, is a carboxyl group or a derivative thereof such as an amide, ester or carboxylate salt derivative, or a group $R_1$; each $R_1$, which may be the same or different, is a hydrogen atom, a hydroxyalkyl group or an optionally hydroxylated alkoxy group; with the proviso that at least two nitrogens carry a —$CHR_1X$ moiety wherein X is a carboxyl group or a derivative thereof, and preferably the provisos that each —$CHR_1X$ moiety is other than a methyl group, and that where Y and Z are —$CHR_1X$ groups at least one $R_1$ is other than hydrogen, and preferably also that each nitrogen atom carrying a —$CHR_1X$ moiety wherein X is a carboxyl group or a derivative thereof carries at least one such moiety which is other than a —$CH_2X$ moiety) and salts thereof.

Particularly preferred as chelating moieties for the paramagnetic compounds of the present invention are the residues of the following: EDTA; DTPA; OTTA; DO3A; DTPA-BMA; DOTA; desferrioxamine; and the physiologically acceptable salts thereof, especially DTPA, DOTA and salts thereof.

Where the chelating moiety in the paramagnetic compounds of the present invention has a labile counterion, that counterion should be a physiologically tolerable ion, for example the ion of an alkali metal, a non-toxic amine (for example tris(hydroxymethyl-)aminomethane, ethanolamine, diethanolamine and N-methylglucamine), a halogen, or a non-toxic organic or inorganic acid.

As the macromolecule component of the paramagnetic compound of the present invention there can be used any of the macromolecules previously suggested for macromolecular paramagnetic MRI contrast agents. Preferably, the macromolecule chosen will be one which is physiologically tolerable and which contains hydroxyl groups or which can be chemically modified to introduce hydroxyl groups or to deprotect protected hydroxyl groups.

Particularly preferably, the macromolecule will be a hydroxyl group containing material selected from the group consisting of polymeric and polymerized carbohydrates and polymerized sugar alcohols and derivatives thereof. The term "polymeric carbohydrate" is used to designate a naturally occurring polymer built up of carbohydrate monomers and the term "polymerized carbohydrate" is used to designate a synthetic polymer obtained by polymerizing carbohydrate molecules, for example with the aid of coupling or cross-linking agents. Similarly the term "polymerized sugar alcohol" is used to designate a synthetic polymer obtained by polymerizing sugar alcohol molecules, for example with the aid of coupling or cross-linking agents.

The macromolecule may thus conveniently be a cyclic or acyclic polysaccharide, such as a glucan, for example starch, amylose, amylopectin (including macromolecular dextrins thereof), glycogen, dextran and pullalan, or a fructan, for example inulin and levan, cyclodextrine or other physiologically tolerable polysaccharides of vegetable, microbial or animal origin.

Examples of polymerized carbohydrates or sugar alcohols which can be used as the macromolecule include so-called polyglucose, which is obtained by polymerization of glucose, and macromolecular products obtained by cross-linking carbohydrates or sugar alcohols (for example mannitol or sorbitol) with at least one bifunctional cross-linking agent, for example epichlorohydrin, a diepoxide or a corresponding halogen hydrin or with a bifunctional acylating agent. An example of such a product which is commercially available is Ficoll (Ficoll is a Trade Mark of Pharmacia Fine Chemicals AB of Uppsala, Sweden) which is obtained by cross-linking sucrose with the aid of epichlorohydrin.

Further examples of substances which can form the basis for the macromolecule include physiologically tolerable derivatives of the polysaccharides mentioned above, for example hydroxyl, carboxyalkyl, acyl or alkyl derivatives, for example hydroxyethyl, dihydroxypropyl, carboxymethyl, acetyl and methyl derivatives of such polysaccharides.

Water-soluble derivatives of insoluble polysaccharides (for example of cellullose) may be considered as well as the water-soluble macromolecules mentioned above. Many such macromolecules are commercially available and/or are extensively described in the literature.

Although the paramagnetic compounds of the invention are particularly suited for use as blood pooling agents when the compounds are soluble and have molecular weights above the kidney threshold, lower molecular weight paramagnetic compounds of the invention may be used in other MRI contrast agents, e.g. agents for investigation of the kidneys, bladder or gastrointestinal tract.

The macromolecule will generally be chosen according to the intended use of the macromolecular paramagnetic chelate. If for example the chelate is to be used in investigation of body cavities having outward escape ducts, for example the gastrointestinal tract, the bladder and the uterus, the macromolecule need not be biodegradable. Furthermore where the chelate is intended for parenteral administration, the macromolecule again need not be biodegradable as long as its molecular weight is sufficiently small as to allow its excretion into the urine. However, where the chelate is to be used in a blood pooling agent it is desirable either to use biodegradable macromolecules whose molecular weights exceed the kidney threshold or to use macromolecular compounds for which each molecule contains more than one macromolecule, for example compounds having a macromolecule-linker-chelate-linker-macromolecule structure. Where a biodegradable macromolecule is to be used, these may for example be macromolecules which are enzymatically degradable by hydrolyses, for example endohydrolases which hydrolyze glycosidic linkages in the macromolecule. Thus for example macromolecules degradable by alpha-amylase, for example starch-based macromolecules, may be chosen.

The macromolecules used for the paramagnetic compounds of the invention may be neutral or may have a net negative or positive charge in solution. For parenteral use, macromolecules with no net charge or with a negative net charge in solution are preferred. A negative net charge may be obtained for example by introducing carboxyl groups or other negatively charged groups into the macromolecules if such groups are not already present therein.

It is particularly preferred that the macromolecule in the compounds of the invention be a polysaccharide and especially preferably a dextran or a derivative thereof, particularly are having a weight average molecular weight of from 40,000 to 500,000 especially about 70,000.

The molecular weight of the paramagnetic compounds of the present invention can easily be selected to suit the particular end use for the compound. As indicated above, this may be done either by selection of appropriately sized macromolecules or by linking together two or more macromolecules to produce the final compound. For general diagnostic purposes, the weight average molecular weight of the paramagnetic compound is preferably in the range of 1,000 to about 2,000,000, preferably 3,000 to about 2,000,000. For the preparation of such paramagnetic compounds, macromolecules of the desired molecular weight can be obtained by conventional methods.

Where it is desired that the paramagnetic compound should be excretable into the urine without prior degradation, the molecular weight is preferably less than 40,000, for example less than 30,000 or more particularly less than 20,000. Where however, the paramagnetic compounds of the present invention are to be used as blood pooling agents, the use to which they are particularly well adapted, the molecular weight of the paramagnetic compound should preferably lie in the range 40,000 to 2,000,000, more preferably 60,000 to 100,000. Where the paramagnetic compound comprises a single macromolecule residue, the molecular weight range limits listed above may be considered to be the appropriate range limits for the molecular weight of the macromolecule also.

In the paramagnetic compounds of the present invention, the paramagnetic metal species, i.e. a paramagnetic metal atom or ion, is preferably non-radioactive and is particularly preferably selected from the group of elements having atomic numbers 21-29, 42, 44 and 57-71, the elements having atomic numbers 24-29 or 62-69 being specially preferred. Examples of suitable lanthanides include gadolinium, europium, dysprosium, holmium, and erbium and examples of other suitable elements include manganese, iron, nickel, chromium and copper. The particularly preferred paramagnetic metal species include Cr(III), Mn(II), Fe(III), Dy(III) and Gd(III), especially Gd and Dy and Cr.

In a further aspect, the present invention provides a process for the preparation of the macromolecular paramagnetic compounds of the present invention, which process comprises admixing in a solvent an at least sparingly soluble paramagnetic metal compound, for example a chloride, oxide or carbonate, together with a macromolecular chelating agent comprising a chelating moiety bound by an amide group to a linker group itself bound by an ester group to a macromolecule, wherein said linker group provides a carbon chain of at least two atoms. between said amide group and said ester group.

The macromolecular chelating agent mentioned in the previous paragraph itself represents a further aspect of the present invention.

Thus in a still further aspect the present invention provides a macromolecular chelating compound comprising a chelating moiety bound by an amide group to a linker group itself bound by an ester group to a macromolecule, wherein said linker group provides a carbon chain of at least two atoms between said amide group and said ester group, or a salt or metal chelate thereof.

The macromolecular chelating agent can itself be prepared by condensing a hydroxyl group containing macromolecule with an amino acid or a salt thereof and reacting the product so obtained with a carboxyl group-, or reactive carboxyl derivative-, containing chelating agent. Thus in a yet still further aspect the present invention provides a process for the preparation of a macromolecular chelating agent according to the present invention which process comprises: reacting a hydroxyl group containing macromolecule with an amino acid or a salt thereof, said amino acid having a carbon chain of at least two atoms between its carboxyl and amine groups, and conveniently being an amino acid of formula I as defined above; reacting the product so obtained with a carboxyl group-, or reactive carboxyl derivative-, containing chelating agent; and, optionally, converting the product so obtained into a salt or metal chelate thereof.

Where the paramagnetic compounds of the present invention are to be administered to the human or non-human animal body as MRI contrast agents, they will conveniently be formulated together with one or more pharmaceutical carriers or excipients. Thus in a further aspect of the present invention provides a diagnostic contrast medium comprising a macromolecular paramagnetic compound according to the present invention together with at least one pharmaceutical carrier or excipient.

The chelating agents and the salts and chelates according to the invention are also useful in other fields in which chelating agents and chelates have been used, for example as stabilizers for pharmaceutical preparation, as antidotes for poisonous heavy metal species and as diagnostic agents for the administration of metal species (e.g. atoms or ions) for radiotherapy or for diagnostic techniques such as X-ray, and ultrasound imaging or scintigraphy. In addition the paramagnetic compounds may also be useful in techniques such as lymph angiography. In a further aspect therefore the present invention provides a diagnostic or therapeutic composition comprising at least one pharmaceutical carrier or excipient together with a metal chelate whereof the chelating moiety is the residue of a chelating compound according to the invention.

In a still further aspect the present invention also provides a detoxification agent comprising a chelating compound according to the invention, optionally in the form of a salt or chelate with a physiologically acceptable counterion, together with at least one pharmaceutical carrier or excipient.

The compositions, e.g. contrast media of the present invention may include conventional formulation aids, for example stabilisers, antioxidants, osmolality adjusting agents, buffers, pH adjusting agents, etc. and may be in forms suitable for parenteral or enteral administration, for example injection or infusion or administration directly into a body cavity having an external escape duct, for example the gastrointestinal tract, the bladder or the uterus. Thus the compositions of the present invention may be in a conventional pharmaceutically administration form such as a tablet, capsule, powder, solution, suspension, dispersion, syrup, suppository, etc; however, solutions, suspensions and dispersions in physiologically acceptable carrier media, for example water for injections, will generally be preferred.

Where the compositions of the invention contain a chelate of a toxic metal species e.g. a heavy metal or radioactive metal ion, it may be desirable to include within the composition a slight excess, e.g. 0.5 to 20 mol %, preferably 1 to 10 mol %, of the chelating compound or of a weaker chelate thereof with a physiologically tolerable counterion, e.g. as discussed by Schering AG in DE-A-3640708 (and AU-A-81889/87).

Where the composition is formulated for parenteral administration, for example where a contrast medium is to be used as a blood pooling agent, a solution in a sterile physiologically acceptable medium, for example an isotonic or somewhat hypertonic aqueous solution would be preferred.

For MRI examination, the contrast medium of the present invention, if in solution, suspension or dispersion form, will generally contain the paramagnetic metal species at a concentration in the range 1 micromole to 1.5 mole per liter, preferably 0.1 to 700 mM. The contrast medium may however be supplied in a more concentrated form for dilution prior to administration. The contrast medium of the invention may conveniently be administered in amounts of from $10^{-4}$ to 3 mmol e.g. $10^{-3}$ to 1 mmol of the paramagnetic metal species per kilogram of body weight, e.g. about 1 mmol Dy/Kg bodyweight.

For X-ray examination the dose of the contrast agent should generally be higher and for scintigraphic examination the dose should generally be lower than for MR examination. For radiotherapy and detoxification conventional doses may be used.

In a yet further aspect, the present invention also provides a method of diagnosis practiced on the human or non-human animal body, which method comprises administering to said body a macromolecular metal chelate, preferably a paramagnetic compound, according to the present invention and generating an X-ray, magnetic resonance, ultrasound or scintigraphic image of at least part of said body.

In a still further aspect the invention provides a method of heavy metal detoxification practiced on the human or non-human animal body, which method comprises administering to said body a chelating compound according to the invention, optionally in the form of a salt or chelate with a physiologically acceptable counterion.

In a yet still further aspect the invention also provides a method of radiotherapy practiced on the human or non-human animal body, which method comprises administering to said body a chelate of a radioactive metal species with a chelating compound according to the invention.

In a still further aspect, the present invention also provides the use of a macromolecular compound or salt or chelate thereof according to the invention for the manufacture of a diagnostic agent for use in methods of image generation, detoxification or therapy practiced on the human or non-human animal body.

As mentioned above, as a result of the use of the particular linker groups, the paramagnetic compounds of the present invention have properties which are particularly improved relative to those of the prior art compounds.

Thus where the paramagnetic chelate GdDTPA is bound directly to dextran, the resulting compound is not stable either in vivo or in vitro. On administration of such a compound, GdDTPA-dextran (molecular weight 70,000) to rabbits, no blood pooling effect was observed and the rapid elimination of the gadolinium into the urine that was observed was very similar to that which is observed for GdDTPA or its salts. In contrast, GdDTPA linked by beta-alanine to dextran of molecular weight 70,000, a compound according to the present invention, is stable in vitro and has almost ideal blood pooling properties insofar as it exhibits a half life in the blood of about 6 hours and has a distribution volume of 0.05 l/kg, a distribution volume which indicates that at least until degradation the distribution of the compound is essentially only within the blood pool.

Nevertheless, the increased blood pooling effect achieved using the amino acid residue linker is not obtained at the expense of ready excretability of the paramagnetic species due to the presence in the paramagnetic compound between the macromolecule and the linker of an ester bond which, unlike the essentially non-biodegradable amide bonds in the macromolecule-linker-chelate compounds of WO-85/05554, is biodegradable.

The disclosures of all of the documents mentioned herein are incorporated by reference.

The following Examples are provide to illustrate the present invention in a non-limiting manner. The products of Examples 1 and 14 are however particularly preferred. The following abbreviations are used herein:

Dextran X: Dextran with molecular weight X. $10^3$ daltons (such dextrans are available from Sigma Chemicals)
DMSO-A: dimethylsulfoxide
DTPA-A: diethylenetriamine pentaacetic acid bisanhydride
ECDI: N-ethyl-N'-(3-dimethylaminopropyl)carbodiimide
FMOC-BA: fluorenylmethyloxycarbonyl-beta-alanine
PP: 4-pyrrolidinopyridine
Water: water deionized by reverse osmosis

EXAMPLE 1

GdDTPA-beta-alanine-dextran (Molecular Weight 70,000)

To a solution of 15.9 g of Dextran 70 in 650 ml of dry DMSO was added 20.3 g of FMOC-BA, 13.7 g of ECDI and 968 mg of PP dissolved in 350 ml of dry DMSO. The reaction mixture was stirred at ambient temperature for 18 hours and 43.1 g of piperidine was added. After 70 minutes, 7.3 ml of concentrated hydrochloric acid was added dropwise, and cooling on an ice/water bath and dropwise addition of 1.7 l of an ether/chloroform mixture (7:3 w/w) yielded a yellow oil. After decantation, the oil was dissolved in distilled water and the pH was adjusted to 4. Sodium chloride was added until the salt concentration was 0.9% in 1400 ml of solution, and the product was dialyzed against 0.9% sodium chloride in water at pH 4 in a hollow fibre cartridge (Amicon HP 10-20) for 24 hours. The solution was then concentrated using the same equipment against distilled water to a volume of 1150 ml, the pH was adjusted to 9 with N-methylmorpholine and 29.18 g of DTPA-A was added while the pH was kept at 8 using the same base. When the solution became clear, the reaction mixture was stirred for 2 hours, 43.78 g of citric acid dissolved in 47.4 ml of 10N NaOH was added, and the pH was adjusted to 6.0 with concentrated hydrochloric acid. 30.37 g of gadolinium chloride hexahydrate dissolved in 200 ml of distilled water was added quickly and the pH was adjusted to 5.5 using 10N NaOH. The solution was dialyzed against distilled water until the relaxation time $T_1$ (determined using a NMR Proton Spin Analyzer, RADX Corporation, Houston, Tex., USA, at 10 MHz and 37° C.) was above 2000 ms. Lyophilization of the solution yielded 15.3 g of a light yellow coloured powder.

ANALYSIS

Elemental analysis: Gd 4.6%; N 2.15%; Na 0.16%; Cl less than 0.01%. Free Gd (xylene orange titration), DTPA, GdDTPA, citric acid, or DMSO (HPLC): less than 0.01% (The percentages in the analysis results are by weight).

The specific relaxation rate $(T_1)$ enhancement (SRRE) (measured in an NMR Proton Spin Analyzer RADX Corp. Houston, Tex., USA at 10 MHz and 37° C.) in distilled water was 9.6 $s^{-1}$ $mM^{-1}$ Gd.

EXAMPLE 2

Injection Solution 78.6 mg of gadolinium (III) DTPA-beta-alanine-dextran (molecular weight 70,000) were prepared in accordance with Example 1 and dissolved in 10 ml of distilled water. The solution was sterile filtered and filled into a 10 ml vial. The solution contained 0.05 mmol Gd/ml.

EXAMPLE 3

Pharmacokinetics in Rabbits

The solution of Example 2 was injected intravenously into three rabbits at a dose of 0.05 mmol Gd/kg body weight. Three other rabbits received gadolinium (III) DTPA-dimeglumine salt intravenously at a dose of 0.05 mmol Gd/kg body weight.

Blood samples were drawn from an ear vein before injection and at 1, 5, 10, 15, 30, 120, 180 and 300 minutes and 24 and 48 hours after injection. Serum was prepared from the blood samples and the relaxation times $T_1$ and $T_2$ were determined in an RADX NMR spectrometer (37° C., 10 MHz). The gadolinium concentration in the serum samples were determined by ICP (inductive coupled plasma). The apparent volume of distribution ($V_D$) and the biological half-life ($t_{\frac{1}{2}}$) were determined using the two-compartment model. The results are as set forth in the Table below:

TABLE

| SAMPLE | $V_D$ (l/kg) | $t_{\frac{1}{2}}$ (hours) |
| --- | --- | --- |
| Gd(III)DTPA-beta-alanine-dextran 70 | 0.05 ± 0.003 | 6.7 ± 0.18 |
| Gd(III)DTPA-dimeglumine | 0.26 ± 0.037 | 0.72 ± 0.11 |

The results presented above show the compound of Example 1 to have a considerably longer half-life than GdDTPA and yet still to be biodegradable as no relaxation effects and no serum gadolinium were observed in serum 48 hours after injection. The observed apparent volume of distribution of 0.05 confirms its blood pooling property.

EXAMPLE 4

Dextran 70-beta-alanine-DTPA 10.0 g of Dextran 70 was reacted with 12.8 g of FMOC-BA, 8.7 g of ECDI, 0.61 g of PP and 31.5 ml of piperidine in 600 ml of dry DMSO and then with 22 g of DTPA-A as described in Example 1 to the point where the citric acid buffer was added. The pH was adjusted to 5.1 and 6M HCl and the solution was dialyzed against 4 l of water. The solution was lyophilized to give 5.5 g of a light yellow solid.

Elemental analysis: N 2.82%, C 42.52%, H 6.74%.

EXAMPLE 5

Dextran 70-beta-alanine-DTPA-Fe (III)

0.5 g of the product of Example 4 was dissolved in 70 ml of water and to this were added 1.38 g of citric acid, 1.49 ml of 10N NaOH and 417 mg of FeCl$_3$ dissolved in 10 ml of water. The pH was adjusted to 5 with 10N NaOH and, after reaction overnight, the solution was dialyzed against water until $T_1$ in the filtrate was above 2000 ms. Lyophilization gave 0.47 g of a light brown solid, 5.5% Fe, relaxivity 0.8 s$^{-1}$ mM$^{-1}$.

EXAMPLE 6

Dextran 70-beta-alanine-DTPA-Dy 0.5 g of the product of Example 4 was complexed with 1.1 g of DyCl$_3$ and isolated as described in Example 5. Yield 0.57 g of a white solid, 9.8% Dy, relaxivity 0.2 s$^{-1}$mM$^{-1}$.

EXAMPLE 7

Dextran 70-beta-alanine-DTPA-Yb 0.5 g of the product of Example 4 was complexed with 1.15 g of Yb(NO$_3$)$_3$ and isolated as described in Example 5. Yield 0.5 g of a yellowish solid, 3.5% Yb, relaxivity 0.03 s$^{-1}$mM$^{-1}$.

EXAMPLE 8

Dextran 70-beta-alanine-DTPA-Cu 0.5 g of the product of Example 4 was complexed with 642 mg of CuSO$_4$ and isolated as described in Example 5. Yield 0.55 g of a light blue solid, 1.5% Cu, relaxivity 0.3 s$^{-1}$mM$^{-1}$.

EXAMPLE 9

Dextran 40-beta-alanine-DTPA-Gd 2.0 g of Dextran 40 was reacted with 2.6 g of FMOC-BA, 1.73 g of ECDI, 122 mg of PP and 6.3 ml of piperidine in dry DMSO as described in Example 1. The product was reacted further with 3.77 g of DTPA-A as described herein, and after complexation in citrate buffer with 3.82 g of GdCl$_3$. 6 H$_2$O the product was dialysed and lyophilized to yield 1.05 g of a white solid, 5.1% Gd, relaxivity 5.1 s$^1$mM$^{-1}$.

EXAMPLE 10

Hydroxyethylstarch-beta-alanine-DTPA-Gd 2.0 g of hydroxyethylstarch (prepared by hydroxyethylation of waxy starch with ethylene oxide according to the method described in U.S. Pat. No. 2,516,634) molecular weight 131,000 and degree of substitution 0.52, was dissolved in 120 ml of dry DMSO. It was reacted with the same reagents in the same quantities and isolated as described in Example 9. Yield 2.3 g of white solid, 5.1% Gd, relaxivity 6.0 s$^1$mM$^{-1}$.

EXAMPLE 11

Dextran 40-beta-alanine-EDTA-Cr 2.0 g of Dextran 40 was reacted as described in Example 9 up to the point where the Dextran 40-beta-alanine water solution had been dialysed at pH 4.2.2.65 g of EDTA-bis-anhydride (prepared using the method of Eckelman et al, J Pharm. Sci., 64 (1975) 704) was reacted with the Dextran-derivative, complexed with 2.74 g of CrCl$_3$. 6 H$_2$O and the product was isolated as described in Example 9. Yield 2.9 g of a purple solid, 3.1% Cr, relaxivity 1.1 s$^{-1}$mM$^{-1}$.

EXAMPLE 12

Dextran 500-beta-alanine-DTPA-Bi 2.0 g of Dextran 500 was reacted as described in Example 9 except that 4.4 g of DTPA-A was used. The reaction mixture was stirred for 3 hours while the pH was kept at 8 with N-methylmorpholine. The pH was then adjusted to 5 with 6N HCl and a buffer solution containing 5.5 g of citric acid and 5.96 ml of 10N NaOH was added. A solution of Bi(III) was prepared by dissolving 3.89 g of BiCl$_3$ in 100 ml of 1M HCl and the pH was adjusted to 7 with saturated ammonia in water. The suspension was centrifuged and the supernatant was decanted off. The precipitate was resuspended and centrifuged twice and the white jelly-like precipitate was added to the buffer solution of the Dextran. The pH was 5.0 and, after reaction overnight, the clear solution was dialysed against 12 l of water and lyophilization yielded 0.8 g of a white solid, 9.4% Bi.

EXAMPLE 13

Dextran 2000-beta-alanine-HEtDTPA-Gd (a) The DTPA-derivative 3,6,9-tris-carboxymethyl-4-(2-hydroxyethyl)-3,6,9-triazaundecane diacid (HEtD- TPA) was synthesized according to the method of PCT/GB88/00572. HEtDTPA trihydrochloride was prepared by loading HEtDTPA on a strong anion ion exhanger and eluting with 1M HCl followed by evaporation. The product was a white solid, mp. greater than 350° C. (decomp.).

Elemental Analysis: Calc.: C 35.14%, H 5.54%, N. 7.69%, Cl 19.45%. Found: C 34.76%, H 5.46%, N 7.74%, Cl 19.56%.

(b) 2.0 g of Dextran 2000 was reacted as in Example 9 to the point before reaction DTPA-A. The solution was lyophilized to yield 1.9 g of a white solid. The product was dissolved in 200 ml of dry DMSO and there were added 2.24 g of HEtDTPA trihydrochloride, 0.86 g of ECDI and 35 mg of PP. After stirring for 24 hours the solution was added to a mixture of 300 ml of ether and 125 ml of $CHCl_3$. The product was isolated by decantation of the supernatant. The product was dissolved in 120 ml of water and the pH was adjusted to 5 with 10N NaOH. To the solution was added a buffer, containing 5.5 g of citric acid and 5.96 ml of 10N NaOH, and then 1.53 g of $GdCl_3 \cdot 6 H_2O$ dissolved in 10 ml of water. The pH was adjusted to 5 with 10N NaOH and after 3 hours the product was dialyzed and isolated as described in Example 9. Yield 2.5 g of a light brown solid, 5.7% Gd, relaxivity 1.4 $s^{-1} mM^{-1}$.

EXAMPLE 14

Dextran 70-beta-alanine-DOTA-Gd (a)
N',N'',N'''N''''-Tetracarboxymethyl-1,4,7,10-tetraazacyclododecane (DOTA)

5.26 g of 1,4,7,10-tetraazacyclododecane (prepared as described by Stetter et al. Tetrahedron, 37(1981)767) was dissolved in 50 ml of water. The pH was adjusted to 10 with conc. HBr, 20.16 g of bromoacetic acid was dissolved in 7 ml of water and a solution of LiOH carefully added with cooling in an ice/water bath. The bromoacetic acid lithium solution was added to the 1,4,7,10-tetraazacyclododecane solution in one portion. The pH was kept between 8 and 9.5 with 4N LiOH while the temperature was gradually increased to 80° C. during 4 hours. After cooling, the solution was mixed with 494 ml of wet Dowex 50WX 4 acidic ion exchange resin in 1.5 l of water and stirred for 1 hour. After thorough washing with water, the gel was washed with 2×750 ml of saturated ammonia. The filtrate was evaporated to yield 10.9 g of a white solid, mp greater than 350° C., FAB-ms M+1 411 and 417 -mono- and dilithium salt. $^{13}C$-and $^1H$-NMR confirmed the structure. 8.72 g of the solid was dissolved in 16 ml of water and the pH was adjusted to 2.5 with conc. HCl. The white solid was filtered off and the process repeated with the evaporated filtrate. The collected solids were dried to yield 4.5 g of a white solid, mp greater than 350° C. (decomp).

(b) Dextran 70-beta-alanine-DOTA-Gd 2.0 g of Dextran 70 was reacted as described in Example 9 to the point before DTPA-A was reacted. The product was lyophilized and dissolved in 100 ml of dry DMSO. 1.66 g of the precipitated DOTA, 0.86 g of ECDI and 62 mg of PP were added and the reaction mixture was stirred overnight at ambient temperature. To the reaction mixture was added a mixture of 150 ml of ether and 62 ml of $CHCl_3$, the white precipitate was isolated by decantation and washing with ether and then dissolved in 80 ml of water. The pH was adjusted to 5 with 10N NaOH and there was added a mixture of 5.5 g of citric acid and 5.96 ml of 10N NaOH and then 0.766 g $GdCl_3.6H_2O$. The reaction mixture was stirred for 50 hours and the product was isolated by dialysis and lyophilization. Yield 2.4 g of a white solid, 7.4% Gd, relaxivity 11.7 $s^{-1}mM^{-1}$.

EXAMPLE 15

Dextran70-5-aminopentanoic acid-DTPA-Gd 5.65 g of 9-fluorenylmethyloxycarbonyl-5-amino-valeric acid (prepared from 5-amino-valeric acid and 9-fluorenylmethyl chloroformate as described by Carpino et al. J. Org. Chem., 37 (1972)3404) was reacted with 2.0 g of Dextran 70, 3.5 g of ECDI and 0.25 g of PP as described in Example 9. The reaction mixture was treated with 12.75 ml of piperidine, the product was isolated and dissolved in water and reacted with 7.44 g of DTPA-A as described herein. The product was complexed with 7.74 g of $GdCl_3.6H_2O$ in citrate buffer and isolated by dialysis and lyophilization as described above. Yield 6.6 g of a light brown solid, 11.4% Gd, relaxivity 5.6 $s^{-1}mM^{-1}$.

EXAMPLE 16

Glycogen-beta-alanine-DTPA-Gd 2.0 g of bovine liver glycogen (Sigma Chemicals) was reacted and isolated as described in Example 9. Yield 2.7 g of a white solid, 7.5% Gd, relaxivity 6.8 $s^{-1}mM^{-1}$.

EXAMPLE 17

Vial containing Dextran70-beta-alanine-DTPA

A vial is filled with 20 mg of Dextran70-beta-alanine-DTPA (Example 4) and 0.2 mg of $Sn(II)Cl_2$ as a dry solid.

A solution of $^{99m}Tc$ as pertechnetate is 0.9% sterile sodium chloride should be added before use. The technetium chelate with Dextran70-beta-alanine-DTPA is for intravenous or subcutaneous administration and is a contrast agent for the vascular system or for lymphangiography.

EXAMPLE 18

Dextran70-beta-alanine-DTPA-Gd and the Calcium-disodium salt of Dextran70-beta-alanine-DTPA 760 mg of Dextran 70-beta-alanine-DTPA (Example 4) was dissolved in 10 ml water and 28 mg of $Ca(OH)_2$ were added. The pH was adjusted with NaOH under ambient conditions. 1 ml of the resulting solution was added to a solution of 1.0 g of Dextran 70-beta-alanine-DTPA-Gd (Example 1) in 9 ml of water, and the resultant solution was sterile filtered, filled into a 20 ml vial and lyophilized.

EXAMPLE 19

Dextran70-beta-alanine-DTPA-Gd and the calcium-trisodium salt of DTPA

To a solution of 1.0 g of Dextran70-beta-alanine-DTPA-Gd (Example 1) in 10 ml of water was added 17 mg of the calcium-trisodium salt of DTPA (Fluka). The solution was sterile filtered, filled into a 20 ml vial and lyophilized.

We claim:

1. A paramagnetic compound comprising a paramagnetic metal species chelated by a chelating moiety bound by an amide group to a linker group itself bound by an ester group to a macromolecule selected from the group consisting of polymeric and polymerised carbohydrates and polymerised sugar alcohols, and physiologically tolerable derivatives thereof, wherein said linker group provides a carbon chain of from 2 to 11 atoms between said amide group and said ester group.

2. A compound as claimed in claim 1 wherein said linker group is a residue of an amino acid of formula I $$HOOC-CH_2-(CHR)_n-NH_2 \qquad (I)$$

wherein, n is an integer of from 1 to 10, and each R, which may be the same or different, represents a hydrogen atom or a hydroxyl, $C_{1-6}$ hydroxyalkyl, or $C_{1-4}$ alkyl group, with the proviso that R on the carbon attached to the amine group does not represent a hydroxyl group.

3. A compound as claimed in claim 2 wherein in formula I n is an integer of from 1 to 10 and R represents a hydrogen atom.

4. A compound as claimed in claim 1 wherein said linker group is a residue of a beta or gamma amino acid.

5. A compound as claimed in claim 1 wherein said linker group is a residue of beta-alanine.

6. A compound as claimed in claim 1 wherein said chelating moiety is a residue of an amino polycarboxylic acid or polycarboxylic acid derivative.

7. A compound as claimed in claim 1 wherein said chelating moiety is a residue of a compound of formula II $$X-CHR_1-NZ-(CHR_1)_2-\underset{\underset{Y}{|}}{N}-(CHR_1)_2-NZ-CHR_1-X \qquad (II)$$

wherein
each of the groups Z is a group $-CHR_1X$ or the groups Z are together a group $-(CHR_1)_2-A'-(CHR_1)_2-$, where A' is O, S, $N-CHR_1X$ or $N-(CHR_1)_p-N(CHR_1X)_2$ where p is 2,3 or 4;
Y is a group $-(CHR_1)_2-N(CHR_1X)_2$ or a group $-CHR_1X$;
each X, which may be the same or different, is a carboxyl group or an amide, ester or carboxylate salt derivative thereof or a group $R_1$;
each $R_1$, which may be the same or different, is a hydrogen atom, a hydroxyalkyl group or an optionally hydroxylated alkoxy group;
with the proviso that at least two nitrogens carry a $-CHR_1X$ moiety wherein X is a carboxyl group or a derivative thereof as defined above, or a salt thereof.

8. A compound as claimed in claim 1 wherein said chelating moiety is a residue of a compound selected from DTPA, DOTA, and salts thereof.

9. A compound as claimed in claim 1 wherein said macromolecule is a polysaccharide.

10. A compound as claimed in claim 1 wherein said macromolecule is a dextran or a derivative thereof.

11. A compound as claimed in claim 10 wherein said macromolecule has a weight average molecular weight of from 40,000 to 500,000.

12. A compound as claimed in claim 1 wherein said paramagnetic metal is of atomic number 21-29, 42, 44 or 57-71.

13. A compound as claimed in claim 12 wherein said paramagnetic metal is Gd, Dy or Cr.

14. A process for the preparation of a macromolecular paramagnetic compound as claimed in claim 1 which process comprises admixing in a solvent an at least sparingly soluble paramagnetic metal compound, together with a macromolecular chelating agent comprising a chelating moiety bound by an amide group to a linker group itself bound by an ester group to a macromolecule selected from the group consisting of polymeric and polymerised carbohydrates and polymerised sugar alcohols, and physiologically tolerable derivatives thereof, wherein said linker group provides a carbon chain of from 2 to 11 atoms between said amide group and said ester group.

15. A macromolecular chelating compound comprising a chelating moiety bound by an amide group to a linker group itself bound by an ester group to a macromolecule selected from the group consisting of polymeric and polymerised carbohydrates and polymerised sugar alcohols, and physiologically tolerable derivatives thereof, wherein said linker group provides a carbon chain of from 2 to 11 atoms between said amide group and said ester group, or a salt of metal chelate thereof.

16. A process for the preparation of a chelating compound as claimed in and claim 15 which process comprises reacting a hydroxyl group containing macromolecule with an amino acid or a salt thereof, said amino acid having a carbon chain of at least two atoms between its carboxyl and amine groups; reacting the product so obtained with a carboxyl group-, or reactive carboxyl derivative-containing chelating agent; and, optionally, converting the product so obtained into a salt or metal chelate thereof.

17. A compound as claimed in claim 1 which is GdDTPA-beta-alanine-dextran.

18. A method of image generation, which method involves administering to a human or non-human animal body an effective amount of a macromolecular metal chelate as claimed in claim 1 and generating a magnetic resonance, image of at least part of said body.

* * * * *